(12) United States Patent
Myers et al.

(10) Patent No.: US 10,517,508 B2
(45) Date of Patent: Dec. 31, 2019

(54) INGESTIBLE BIO-TELEMETRY COMMUNICATION NETWORK AND ASSOCIATED SYSTEMS

(71) Applicant: etectRx, Inc., Gainesville, FL (US)

(72) Inventors: Brent Arnold Myers, Palm Bay, FL (US); Judd Sheets, St. Petersburg, FL (US)

(73) Assignee: etectRx, Inc., Gainesville, FL (US)

( * ) Notice: Subject to any disclaimer, the term of this patent is extended or adjusted under 35 U.S.C. 154(b) by 0 days.

(21) Appl. No.: 15/454,927

(22) Filed: Mar. 9, 2017

(65) Prior Publication Data

US 2017/0258362 A1   Sep. 14, 2017

Related U.S. Application Data

(60) Provisional application No. 62/306,528, filed on Mar. 10, 2016.

(51) Int. Cl.
| | | |
|---|---|---|
| *A61B 5/07* | (2006.01) |
| *H04B 5/00* | (2006.01) |
| *H04Q 9/14* | (2006.01) |
| *H04W 56/00* | (2009.01) |
| *H04W 72/04* | (2009.01) |

(Continued)

(52) U.S. Cl.
CPC ............ *A61B 5/073* (2013.01); *H04B 5/0037* (2013.01); *H04L 67/12* (2013.01); *H04Q 9/14* (2013.01); *H04W 4/80* (2018.02); *H04W 52/0216* (2013.01); *H04W 56/002* (2013.01); *H04W 72/0453* (2013.01); *H04W 74/085* (2013.01); *A61B 2560/0219* (2013.01); *H04B 1/713* (2013.01); *H04Q 2209/40* (2013.01);

(Continued)

(58) Field of Classification Search
CPC ............ A61B 5/073; A61B 2560/0219; H04B 5/0037; H04B 1/713; H04W 52/0216; H04W 72/0453; H04W 4/80; H04W 74/085; H04W 56/002; H04Q 9/14; H04Q 2209/40; H04L 67/12
See application file for complete search history.

(56) References Cited

U.S. PATENT DOCUMENTS

2007/0060976 A1* 3/2007 Denzene ............ A61N 1/37252
607/60
2014/0309505 A1* 10/2014 Euliano ................ A61B 5/4833
600/302

FOREIGN PATENT DOCUMENTS

WO    2010107980    9/2010

* cited by examiner

*Primary Examiner* — Brian Wilson
(74) *Attorney, Agent, or Firm* — Bass, Berry & Sims, PLC

(57) ABSTRACT

Ingestible bio-telemetry communication network and associated systems are described. The communication network can include one or more ingestible bio-telemetry tags; and a reader, wherein each of the one or more ingestible bio-telemetry tags generates an out-link signal comprising, for each bit of data in a frame, a pulse reverse keyed symbol. Multiple ingestible bio-telemetry tags can be managed at the same time by allowing the frequency of the transmit carrier signal to change, or "hop" to different frequencies so as to minimize likelihood of collision. A reader can identify the proper frequency either by a signal from the tags indicated the frequency of the next hop or, when no bi-directional communication is available, by deducing the carrier signal frequency from the start bits of a received frame from the tag and scanning for the shifted carrier signal frequency within a tolerance of the deduced carrier signal frequency.

7 Claims, 16 Drawing Sheets

(51) Int. Cl.
*H04W 74/08* (2009.01)
*H04W 52/02* (2009.01)
*H04L 29/08* (2006.01)
*H04W 4/80* (2018.01)
*H04B 1/713* (2011.01)

(52) U.S. Cl.
CPC ............ *Y02D 70/00* (2018.01); *Y02D 70/142* (2018.01); *Y02D 70/166* (2018.01); *Y02D 70/42* (2018.01)

$Px3(Hn) = 1 - Pc3^{Hn}$   $Pc3 = 0.505$

Px3 is the probability that at least 1 of the Hn slot hops have no collisions $Px1(Hn) = 1 - Pc1^{Hn}$

| C1 | C0 | Dual Mode (Mode Pin Low) | | |
|----|----|----|----|----|
| | | SET (4 bits) | DSYNC DSEND (2 bits) | |
| 0 | 0 | May tune broadcast TX Frequency | Used for Frame Sync | |
| 0 | 1 | May tune broadcast TX frequency | Used for Frame Sync | |
| 1 | 0 | Used for test vector input (6 bits) | | |
| 1 | 1 | Used for test vector input (6 bits) | | |

Start: Test sequence begins. Reader sends in-link and orients. TAG powers up.
A: Start of first full mode 0 frame
B: Command that Broadcast switch is 2 frame delay (788mS). Send out mode 2 frames and detect IC in parallel is performing BIST operation
C: In-link commands BIST test mode output and transmit PAM at 1 burst/bit. In-link test vectors optional RF Power burst time multiplexed with out-link burst synced by test reader External burst cap will hold chip power between power bursts

| Pin Name | Description |
|---|---|
| Mode | TAG Mode Select |
| d0 | TAG Address 0 |
| d1 | TAG Address 1 |
| d2 | TAG Address 2 |
| LF+ | In-Link sensing input |
| LF- | TAG Reference level (Ground) |
| Vbat | Positive electrochemical battery input |
| HF+ | TX Out-link positive antenna port |
| HF- | TX Out-link negative antenna port |

INGESTIBLE BIO-TELEMETRY COMMUNICATION NETWORK AND ASSOCIATED SYSTEMS

BACKGROUND

Non-compliance of patients with drug regimens prescribed by physicians can cause a multiplicity of problems, including negative patient outcomes, higher healthcare costs and an increased risk of the spread of communicable diseases. Other areas where compliance can be critical is in, for example, pharmaceutical clinical trials, geriatrics and mental health/addition medicine. It is beneficial, then, to provide compliance monitoring. Compliance monitoring can take the form of direct observance or in vivo biotelemetry and monitoring.

BRIEF SUMMARY

Ingestible bio-telemetry communication network and associated systems are described that may significantly improve the reliability and cost effectiveness of electronic drug adherence telemetry systems. Communication protocols, including supporting circuitry and testing are also described.

An out-link communication format is provided, referred to herein as "pulse reversal keying", which includes a fixed relationship between transmitted burst frequency and pulse spacing. The pulse reversal keying format can assure 50% or more burst density regardless of data, allow for dynamic tuning (which can improve receiver performance), and can simplify frame synchronization by providing a unique but short start sequence.

An ingestible bio-telemetry tag ("TAG") can generate an out-link signal comprising, for each bit of data in a frame, a pulse reverse keyed symbol formed of a burst containing a total of N pulse slots, where a logic 1 has N1 leading pulses and N0 trailing pulses, and a logic 0 has N0 leading pulses and N1 trailing pulses, wherein pulse spacing is directly related to a transmit carrier period for a transmit carrier signal. In one implementation, a controller (which may be referred to as a master digital control and program circuit) on a TAG can provide a gating signal used to modulate a TX carrier with the appropriate pulse reverse keyed symbol based on data content (e.g., which may be stored on the IC and may include patient ID or medication type). The gating sets the pulse spacing of the bursts. The gating is controlled by the on-chip clock derived from an in-link signal reference which is also used to phase lock and frequency scale the TX carrier to a desired operating frequency.

A communication protocol is provided that includes bi-directional (command mode) and unidirectional (broadcast mode) telemetry of data so that data can be received from TAGs even when bi-directional communication is not available.

A multiple ingestion methodology is provided in which TAGs perform multiple frequency hops to reduce a chance of collision. Multiple ingestible bio-telemetry tags can be managed at the same time by allowing the frequency of the transmit carrier signal to change, or "hop" to different frequencies so as to minimize likelihood of collision. The broadcast methodology, which exploits the undesired characteristic of poor frequency tolerance of IC technology, includes, while in the broadcast mode, allowing the transmit frequency of a pill to randomly change within a frequency region. The scanning methodology reducing the number of channels to be scanned includes analyzing the pulse period at the reader (when configured as described with respect to the broadcast format of pulse reversal keying) at a start of a frame to deduce the transmit frequency of a TAG, and, when needed, retune to the carrier frequency being scanned accordingly.

The communication protocol having the command mode and broadcast mode can also provide information about the NEXT hop location. For example, the broadcast methodology, while a TAG is in the command mode, includes using the in-link signal from a reader to provide a time sync pulse and transmitting a burst at a random time relative to the sync pulse. The time slot the tag transmits (as the NEXT hop location) can be determined by a random number generator within each TAG and the TAG randomly hops from one slot to another, until an in-link command freezes a TAG to a slot. Accordingly, a reader can identify the proper time slot to receive an out-link signal from a TAG either by a signal from the TAG indicating the time slot of the next hop or, when no bi-directional communication is available, by deducing the carrier signal frequency from the start bits of a received frame from the tag and scanning for the shifted carrier signal frequency within a tolerance of the deduced carrier signal frequency.

A test methodology and protocol is also provided. A low cost test platform can include a tank holding TAGs to be tested, a test chute connected to the tank and having RF coils adjacent a region, a gate allowing a single TAG at a time to pass through the test chute to undergo test while being powered by the RF coils, and a Bin control that moves the tested TAG to an appropriate bin based on the success of the test. The TAG includes BIST circuitry and a power source that does not activate an electrochemical battery on the TAG.

A test sequence is provided that utilizes the bi-directional communication circuitry of a TAG to carry out a test with minimal test time. The test sequence begins with initialization where the reader sends an in-link and the TAG powers up. A first full mode 0 frame (corresponding to command mode) is sent by the in-link. Then the reader sends a command to the TAG so the TAG will identify a lost in-link upon a 2 base frame delay. The reader then stops communicating (in-link is removed), and this should cause the TAG to operate in broadcast mode. The reader waits the time for two full frames to be sent with associated frequency hopping to determine whether broadcast mode is operational. The reader can determine whether broadcast mode was a success and, in response to receiving a command from a re-established in-link, the TAG can send the BIST data on digital functions obtained during the prior sequence.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 5A illustrates the segmentation of a span into five regions and FIG. 5B illustrates a further segmentation with possible spectral breakdown.

DETAILED DESCRIPTION

Ingestible bio-telemetry communication network and associated systems are described that may significantly improve the reliability and cost effectiveness of electronic drug adherence telemetry systems.

Certain implementations described herein can address physiological impairments which restrict signal propagation. Certain implementations described herein can address poor intrinsic frequency stability of the ingested integrated electronics (the "TAG"). Certain implementations can overcome limitations of the devices with respect to multiple pill ingestions. Certain implementations can address the test complexity of the monitoring TAG.

Figure 1:
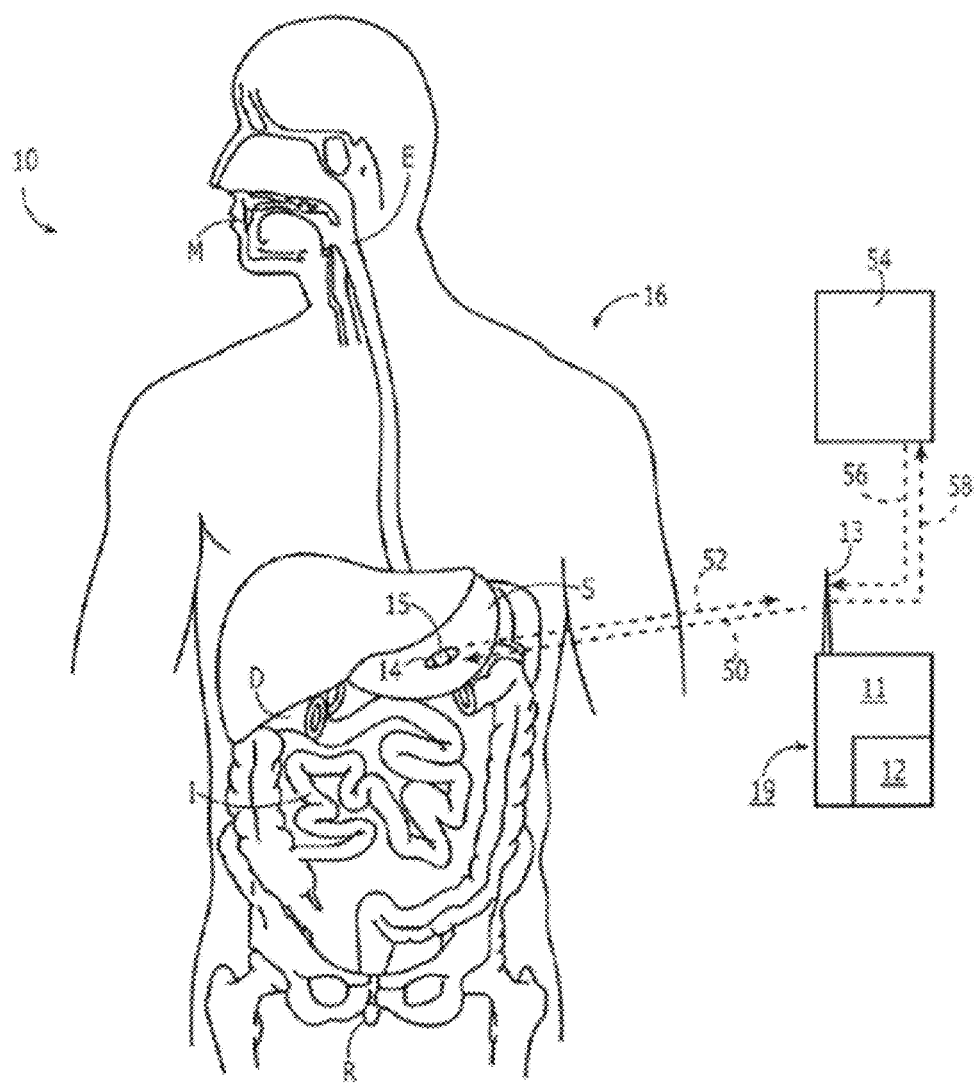
FIG. 1 illustrates a compliance monitoring system for drug adherence.

FIG. 1 illustrates a compliance monitoring system for drug adherence. Referring to FIG. 1, a system 10 for monitoring medication compliance in a patient 16 includes an electronic sensor 11, preferably in the form of an external wireless monitor or reader 11 that includes an RF transceiver 12 and one or more antennas 13. The antenna 13 can be external or internal to the reader 11 and can be implemented in a variety of ways as known in the art, including an on-chip antenna or simple pads or electrical contacts that function as an antenna. The reader 11 detects the presence of an electronic pill 14 in, for example, the gastrointestinal (GI) tract of the patient 16. As shown, the electronic pill 14 has a TAG 15 that is attached to or part of the pill 14. For purposes of this disclosure, the term "pill" can include a capsule or other form of medication administration or testing. The system 10 is designed to detect the pill 14 when located in the patient's mouth M, esophagus E, stomach S, duodenum D, intestines (including the colon) I or rectum R.

As mentioned above, the system 10 includes a TAG 15 fixed with the pill 14, either internally or along the outer surface, or both. After ingestion of the pill 14, the tag 15 can become or be made electronically active and begins communication with the external reader 11. The external reader 11 may be in a housing 19 worn by or attached with the patient 16 so as to be comfortable and easy to wear continuously to ensure it is always with the patient.

The electronic pill 14 comprises an orally ingestible and biocompatible drug-transporting device with embedded or attached electronic circuits (the TAG 15) that communicates with the external wireless reader 11. The electronic pill 14, and more particularly the TAG 15, has, for example, a silicon-based integrated circuit and/or other passive components such as coil antennae and capacitors. The circuit can incorporate millions of transistors, patterned through various semiconductor processing steps, to provide an enormous amount of intelligence. For instance, the electronic pill 14 can store a patient's medical history in addition to detailed information about a drug being administered, provide a unique identification number, and implement advanced communication circuits and protocols to reliably transmit data to the external wireless reader 11.

In use, one or more electronic pills 14 may be taken by a patient 16. The data reader 11 and the one or more TAGs 15 can exchange bidirectional data 50/52. The reader 11 may probe the one or more TAGs 15 inside the patient 16 and coordinates, when possible, the communication between the possibly multiple TAGs 15 and the reader 11. Multiple ingested tags may communicate simultaneously, sequentially, or in other ways.

The TAGs 15 communicate their unique identification data and, in some cases, whether they are in the GI tract. The reader 11 can provide output data 58 to a user interface 54 such as a laptop or smartphone enabling, in some implementations, real-time upload of medication events to a remote database or other location. The reader 11 may receive, via the channel 56, information from the user interface 54 indicating medication regimen status such as the time of the next scheduled medication event, confirmation of the event from the main database, or other information from the user interface 54 or the remote database or trial coordination center via a wide area network (cell or Wi-Fi network) channel. In some cases, the user interface 54 and reader 11 are embedded into a single device, either on or off the body.

The data link from the reader 11 to tag 15 is defined as the "in-link" path 50. In-link data to the tag may include, but not be limited to, at least one of synchronization, signaling, address, and tag configuration information. The reader 11 may transmit information by way of differential metallic skin contacts. The in-link signal 50 passes through the body of patient 16 and can be sensed by the TAG 15 through a differential probe network.

The data link from the TAG 15 to the reader 11 is defined as the "out-link" path 52. Out-link data to the reader may include, but not be limited to, at least one of GI sensing, pharmaceutical, adherence, signal level, physiologic data, biometric identification data, and address information. The out-link channel 52 is a radio frequency signal traveling through both the body of the patient 16 and the free space between the body and the antenna of the reader 11. A small antenna on the TAG 15 radiates the out-link signal 52 which is received at the reader 11. The reader 11 can be capable of receiving signals 52 from multiple tags 15 simultaneously. System 10—with TAGs 15 and reader 11 works together to complete a system that can accurately detect a medication event, including the time of ingestion, the dosage, and specific identification of the medication and/or subject using the system. This information is then used to verify critical compliance with drug therapy. This data can also be used in combination with other patient data to improve adherence and treatment outcomes.

As illustrated in FIG. 1 and described above, a compliance monitoring system can be a bi-directional telemetry system providing an in-link signal and an out-link signal. An in-link signal is a synchronizing signal that is transmitted from a patch or other injection mechanism to an ingested TAG. An out-link signal is generated by the TAG by using the received synchronizing signal. The out-link signal is a frequency stable, outbound telemetry signal that incorporates the desired telemetry data (medication type, dosage, serial number, etc.). The TAG can generate the out-link signal by phase locking to the in-link signal that provides a stable time base. This approach avoids the addition of costly and area consuming time base circuitry on the TAG (crystal or other precision component). In addition, the time base from the in-link signal may also be used to multiplex several TAG transmissions and thus provide a means for multiple pill ingestions in a straight-forward manner.

In real world applications, there may be times where the in-link signal is not detectable for physiologic or other reasons. There may also be situations where it is not convenient to use a patch or other signal injection method and thus an in-link signal may not exist at all. The described systems and techniques enable a TAG to broadcast telemetry data in the absence of an in-link signal while still providing a mechanism to allow multiple ingestions.

Figure 2A:
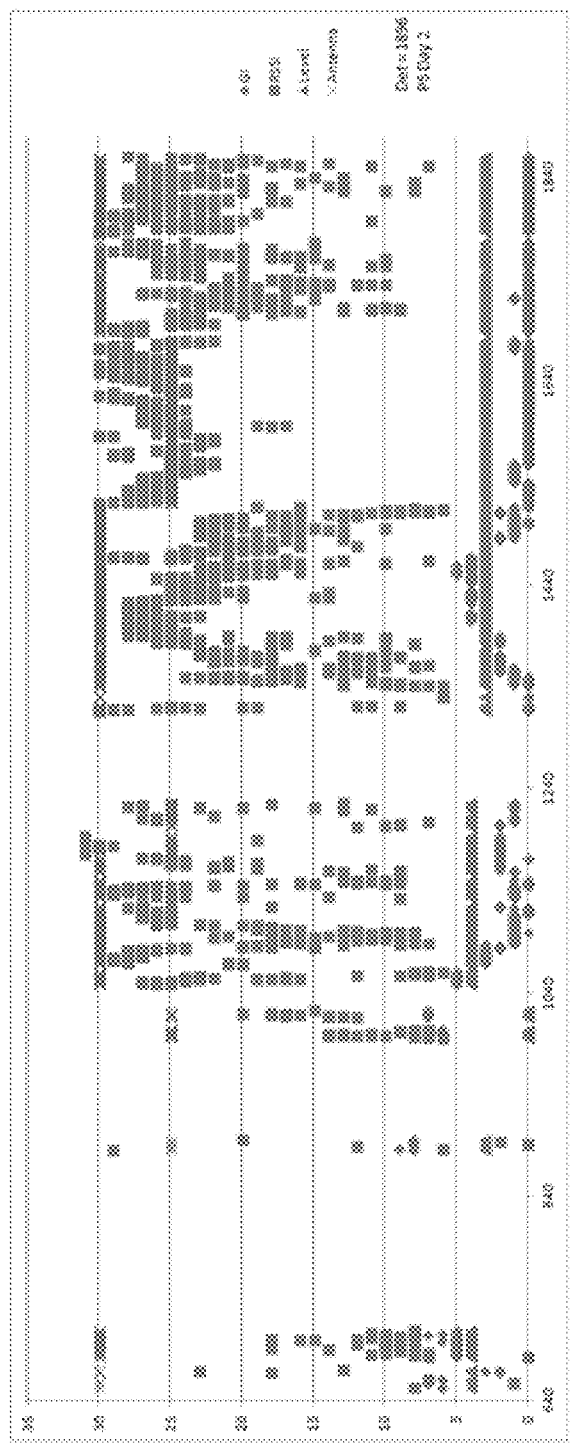
FIGS. 2A and 2B illustrate in-link signal strength and out-link frequency variation in the absence of In-link reference.
Figure 2B:
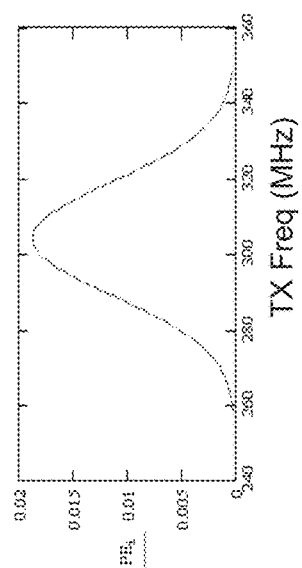

FIGS. 2A and 2B illustrate in-link signal strength and out-link frequency variation in the absence of In-link reference when the described systems and techniques are not used. FIG. 2A shows the received signal strength of an in-link signal as seen by a real ingested TAG (e.g., such as described by application Ser. No. 14/573,315 entitled "Electronic Medication Compliance Monitoring System and Associated Methods"). The shape corresponding to the label RSSI (boxes), and circled in the plot, indicates the signal power of the in-link signal over time. As can be seen, the signal varies significantly. In fact, there are gaps in reception where no telemetry data is provided by the TAG. These gaps are due to the loss of in-link. In-link loss can be caused by several factors including positioning in the stomach where in-link may not be present, or TAG rotation in which the in-link receptor pads may not be in proper orientation to sense the in-link signal, or stomach peristalsis which compresses or lifts the TAG such that the in-link signal is not detectable. In such cases there would be loss of data.

Furthermore, with no in-link signal present the TAG has no time reference to generate a stable transmit signal. Instead, the TAG must rely on integrated components such as resistors, capacitors, inductors, or transistor characteristics to set a time base. It is well known that these component variations are significant and ultimately lead to a time base that cannot be controlled to better than 15% or more. As an illustration of this effect, FIG. 2B shows the frequency distribution of a ring oscillator based transmitter tuned to a mean frequency M of 303.5 MHz. This data is based on actual measured performance. The oscillation (or transmit frequency) has a normal distribution with a variance of 15 MHz (M=303.5; σ=15). This corresponds to about a 90 MHz spread of potential carrier frequencies.

A significant issue with this wide variation is the effort required to receive the out-link telemetry. Since the transmit frequency is not known in advance the receiver must search for the signal. Search time is critical since the longer the receiver is activated the shorter the lifetime of the receiver when utilizing battery power. Further, since no accurate time-base is available, coherent demodulation techniques are impractical thus requiring use of amplitude based modulation. In cases where long series of binary data zero is transmitted there will be a lack of transmit data for the receiver to recover and lock to.

The above described issues are exacerbated when monitoring compliance with multiple ingestions. For example, in the case where the in-link signal provides a time base which will synchronize multiple TAGs, a random transmit timeslot can be generated on each TAG to assure that there is low likelihood of any two TAG's transmitting in the same slot. However, in the absence of in-link, there is no means to assure that two or more TAGs ingested simultaneously will not interfere and cause data errors.

Communication protocols are described herein that can address the above outlined problems. The described systems and techniques enable the TAG to sense loss of in-link and switch to a broadcast mode of telemetry data. In addition, a communication protocol is provided that minimizes reception time while maximizing likelihood of detection. Moreover, a communication protocol and associated algorithms are provided that permit multiple ingestions with very low probability of collision whether in-link is present or not. The entire protocol (combining the various components herein) can handle both the case where in-link is present and when it is not. For definition purposes, "command mode" defines bi-directional communication when a robust in-link is present, and "broadcast mode" is defined when no in-link signal is available.

Figure 3:
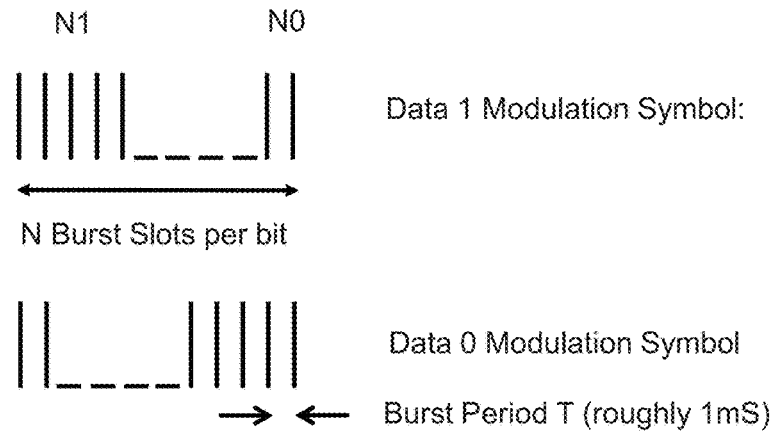
FIG. 3 illustrates a modulation format for a TAG of the ingestible bio-telemetry communication network described herein.

The out-link signal can be a series of pulse modulated radio frequency (RF) signals of duration typically 1 to 2 microseconds and period of roughly a millisecond. This is about a 1 to 1000 duty cycle which means the signal is absent far more than it is present. The pulses are present based on a modulation scheme of some type. For example, the presence of a pulse may represent a transmitted data bit of one while the absence of a pulse is data zero. To improve signal to noise ratio, the pulses may be arranged such that N pulses represent data one. N may be five for example. The lack of N pulses would represent a zero. If there is a long string of data zeros this implies a long period where no out-link pulses occur. Such a situation would mean the receiver has no energy with which to maintain a signal lock and out-link may be lost. To overcome this, a "pulse reversal keying" modulation format can be utilized as shown in FIG. 3. Here, the modulation symbol representing a logic 1 consists of N1 leading pulses and N0 trailing pulses with open slots in between.

For pulse reversal keying, the leading and trailing edge pulses representing a logic one are reversed for a logic zero. For example, as shown in FIG. 3, a logic one (Data 1) is shown with 2 trailing pulses (N0) and 5 leading pulses (N1) in a burst sequence for the case of N=10. For the logic zero (Data 0), the sequence is reversed. It can be shown that the detection optimum is achieved when N0=0 and N1=N/2. Marks represent points in time where pulses are present and spaces represent points in time where pulses are absent. Regardless of data content, pulses will be present with 50% density making synchronizing possible with any data string. A critical aspect of the modulation format is that by design the pulse spacing is directly related to the transmit carrier period in both command and broadcast modes. Once detected, this information can be used to determine the exact carrier frequency (particularly in broadcast mode). Such information may be used to fine tune the out-link receiver and improve the signal to noise ratio.

Figure 4:
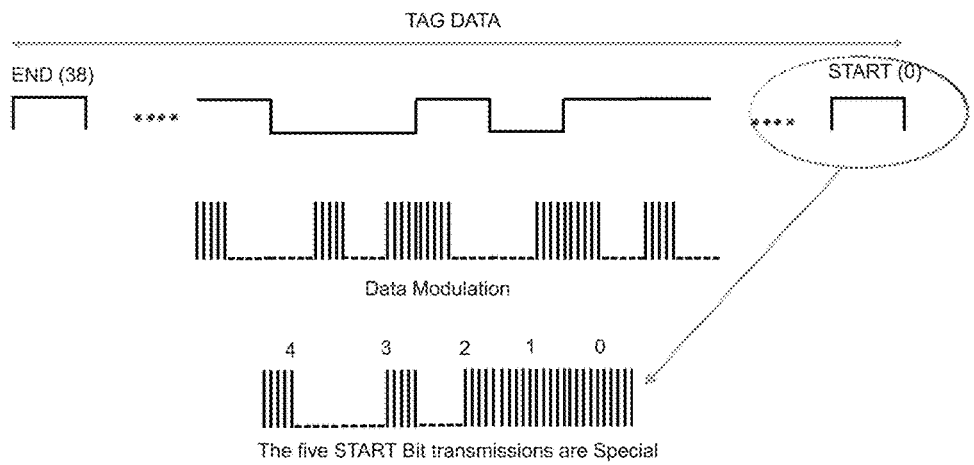
FIG. 4 illustrates an example frame encoding.

FIG. 4 shows an example frame sync sequence, including frame encoding for 39 bits of data. The special frame sync sequence allows the receiver to easily distinguish a frame start without the need for a data correlator. The frame start sequence is unique in that in could never occur in any other data grouping. In particular, for the example unique sequence shown in FIG. 4, it can be seen that bit 0 and bit 1 are entirely composed of pulses, which cannot occur using the encoding of pulse reversal keying. Advantageously, reducing START bit length reduces total frame transmission time.

Figure 5A:
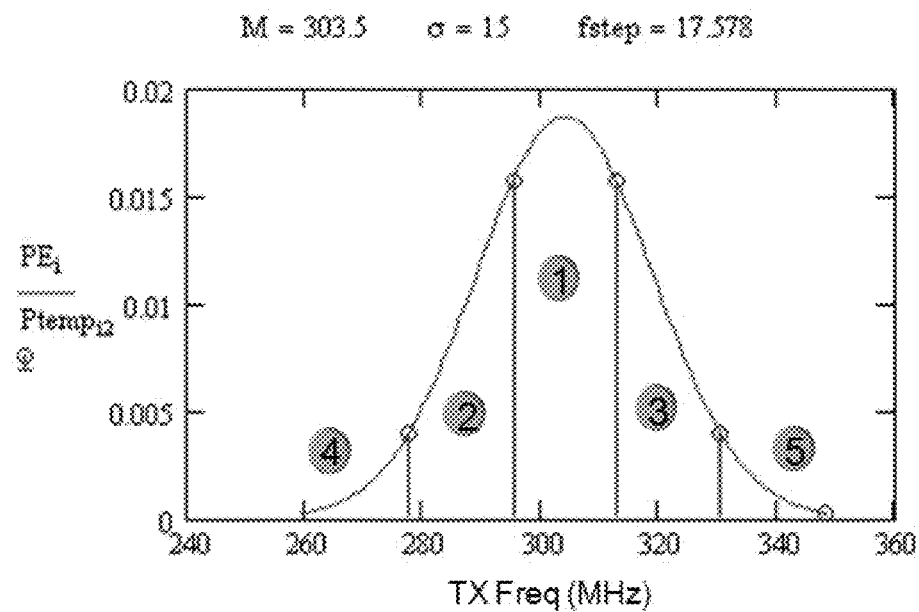
FIGS. 5A and 5B illustrate segmentation of broadcast transmission frequencies.
Figure 5B:
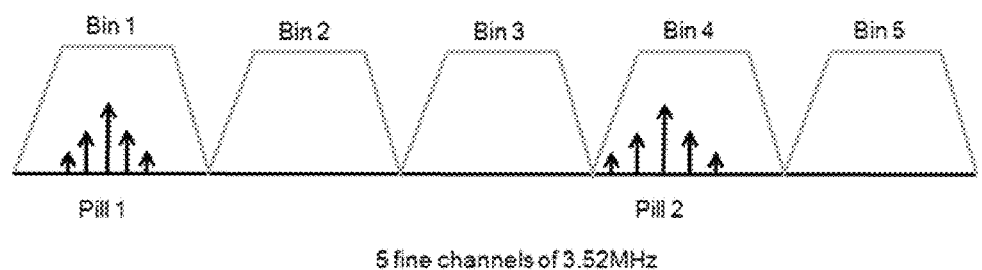

When transmitting in broadcast mode there is no a priori knowledge of the transmit frequency. As mentioned with respect to FIG. 2B and again illustrated in FIG. 5, the possible transmit frequencies span 90 MHz with a normal distribution. With a 1 μs pulse width, this corresponds to a transmit bandwidth of 318 kHz. Hence, over a span of 90 MHz there are 282 possible transmission channels. The receiver must be capable of determining if a burst occurs in any of these channels. The out-link receiver could scan across the channels which is time consuming, or look at each channel in parallel which is hardware and cost prohibitive. A compromise solution is to recognize that while the span is large, the majority of TAGs will transmit close to the average of 303.5 MHz. As illustrated in FIG. 5A, if the span is broken into 5 regions of about 18 MHz each then there is a 45% chance that any pill will fall in the center region (1) and 48% that it would fall in regions (2) or (3). Looking in these regions first will yield the fastest detection time on average. A detection bandwidth of 18 MHz will yield a poor signal to noise ratio (SNR) however and also in multiple ingestion scenarios the chance of two or more transmissions falling in region (1) would be quite high. Such a collision would lead to bit errors. The compromise is to break each region into yet smaller regions and process each of these in parallel. For example, each region could be split into five equal bins of about 3.6 MHz, such as illustrated in FIG. 5B.

When multiple ingestions occur, the detection requirements increase in complexity. Since it is possible that a single patient could take several doses or types of medication at the same time, the likelihood of transmission overlap is greater with each increase in the number of simultaneous ingestions. In the command mode this problem is solved by using the in-link signal as a means to provide a time sync pulse and have each pill transmit a burst at a random time relative to the sync pulse. The time slot the TAG transmits in is determined by a random number generator within each TAG. Each TAG will randomly hop from one slot to another, until an in-link command freezes a TAG to a slot. It is completely up to the in-link controller to freeze a TAG or not. But once a TAG is frozen to a time slot it remains there for the remainder of its lifetime.

In broadcast mode there is no time base available. Fortunately, there is an intrinsic multiplexing mechanism via the relative frequency variability of the transmit frequency from one TAG to another. This is clear by referring to FIG. 5B where pill 1 and pill 2 fall in different frequency bins. However, there is still a likelihood of two or more pills colliding in any frequency bin, particularly as the number of ingestions increase. It can be calculated what the likelihood of collision is for the situation in FIG. 5B.

Figure 6:
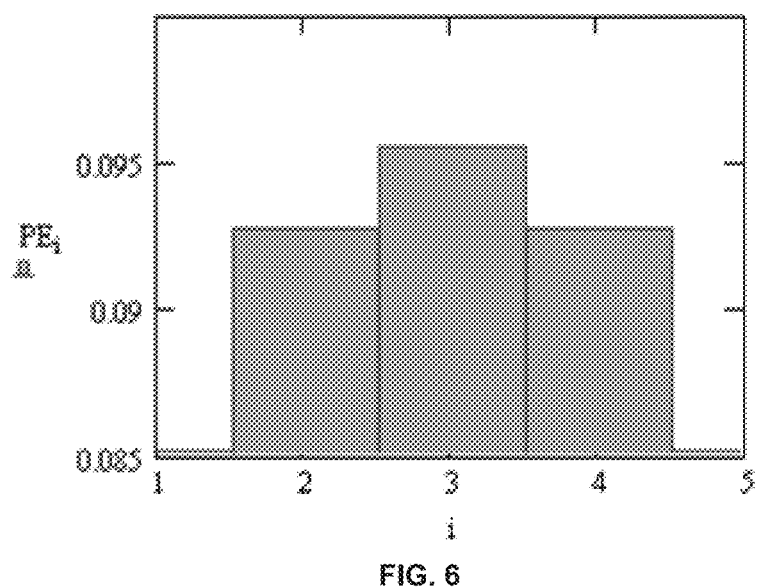
FIG. 6 illustrates a graph of pill occupancy distribution for a scan of Region 1.

The probability for each of the five bins in region 1 (each of bandwidth 3.6 MHz) that a pill transmission will occur can be seen in FIG. 6. For example, the probability that a transmission could occur in bin 1 or bin 5 of region 1 is 0.085. For the case that 5 simultaneous transmissions occur, it can be shown that the chance that at least 2 occupy the same transmission bin (3.6 MHz) within region (1) is 21%. In particular, the probability of at least 2 of k pills colliding in region 1 (N bins): for k=5, N=5 is as follows.

$$PE = \begin{pmatrix} 0 \\ 0.085 \\ 0.093 \\ 0.096 \\ 0.093 \\ 0.085 \end{pmatrix} \quad \sigma = 15$$

$$Pc1 := \frac{1}{1 + \frac{k-2}{N}} \sum_{i=1}^{N} \left[ 1 - \left[ (1 - PE_i)^k + \frac{k \cdot PE_i}{(1 - PE_i)^{(1-k)}} \right] \right] \quad Pc1 = 0.212,$$

where PEi is the probability of any single TAG transmitting in bin i. It should be noted that pills may fall outside of region 1 in which case those would be processed in another region.

A 21% chance of at least 2 pills occupying the same transmission bandwidth (bin) is unacceptably large. While the chance of collision could be reduced if the fine bandwidth were reduced below 3.6 MHz, reducing the fine bandwidth is costly in hardware. According to an implementation described herein, the transmit frequency of each pill is allowed to randomly change within Region 1. In other words, the transmissions of a TAG are allowed to randomly hop between the fine bandwidths shown in FIG. 5B. Interestingly, as illustrated in FIG. 7, after some number of random hops, the chance that at least one of those hops resulted in no transmission overlaps is quite high.

Figure 7:
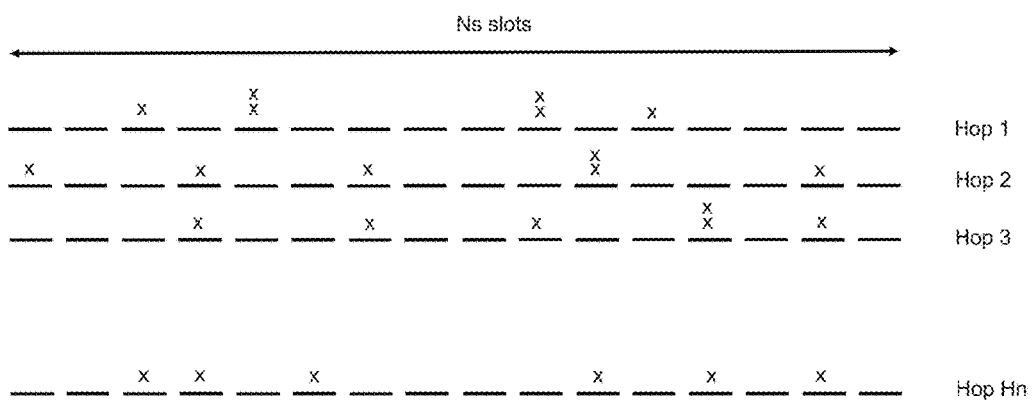
FIG. 7 illustrates a multiple pill slot concept for 6 pill ingestions.

Referring to FIG. 7, the slots may represent either time (as in command mode) or frequency (as in broadcast mode). As time progresses (vertically from top to bottom in the figure), it can be seen that eventually there is a sample in the ensemble where no collisions occur. During that sample, each pill will be detected uniquely with no collisions. It is a simple matter of inventory control to separate out the messages. Accordingly, for the case shown in FIG. 8, the bins represent either time or frequency slots that a pill (x) may occupy. In command mode, the time slots have equal probability of being populated. In broadcast mode, the frequency slots have normal probability of being occupied. Over several hops there is a high probability that at least one of the ensemble will have no slot collisions.

Figure 8A:
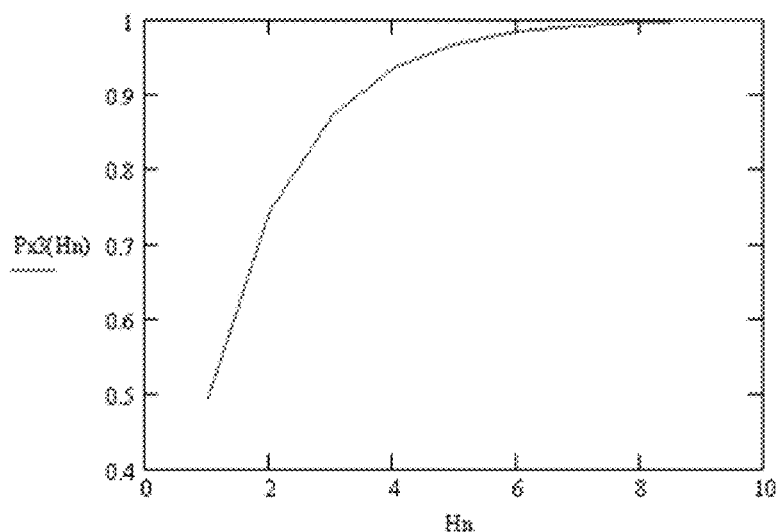
FIGS. 8A and 8B show plots of the collision probability for the collision control methodology in command mode (FIG. 8A) and in broadcast mode (FIG. 8B).
Figure 8B:
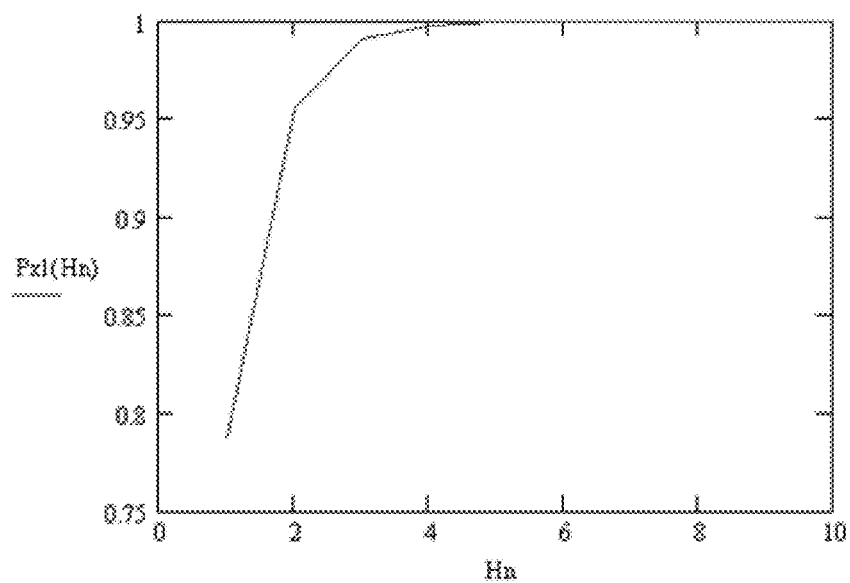

FIGS. 8A and 8B show plots of the collision probability for the collision control methodology in command mode (FIG. 8A) and in broadcast mode (FIG. 8B). Consider the case of the command mode where there are 64 possible time slots. It is easily calculated the chance of collision as the number of random slot hops (Hn) occur. For example, as shown in the plot of FIG. 8A, if 10 pills are taken at once the probability of collision Pc3 is 0.505, but after only 8 random hops, the chance that one of those hops yields no collisions approach's unity. Since there is no limit (other than time) on the number of hops that could occur, there is virtual certainty that all pills will be detected eventually. This is true until the number of pills approaches the number of available slots which practically is not likely to happen.

For the broadcast mode, as illustrated in the plot of FIG. 8B when there are 5 pills taken, the probability of collision for any single hop is Pc1=0.217, but after only 4 hops the chance of unique detection is near unity. Hence, by introducing a hopping mechanism into the transmission protocol, a means to support a large number of ingestions without additional hardware support is apparent.

Figure 9:
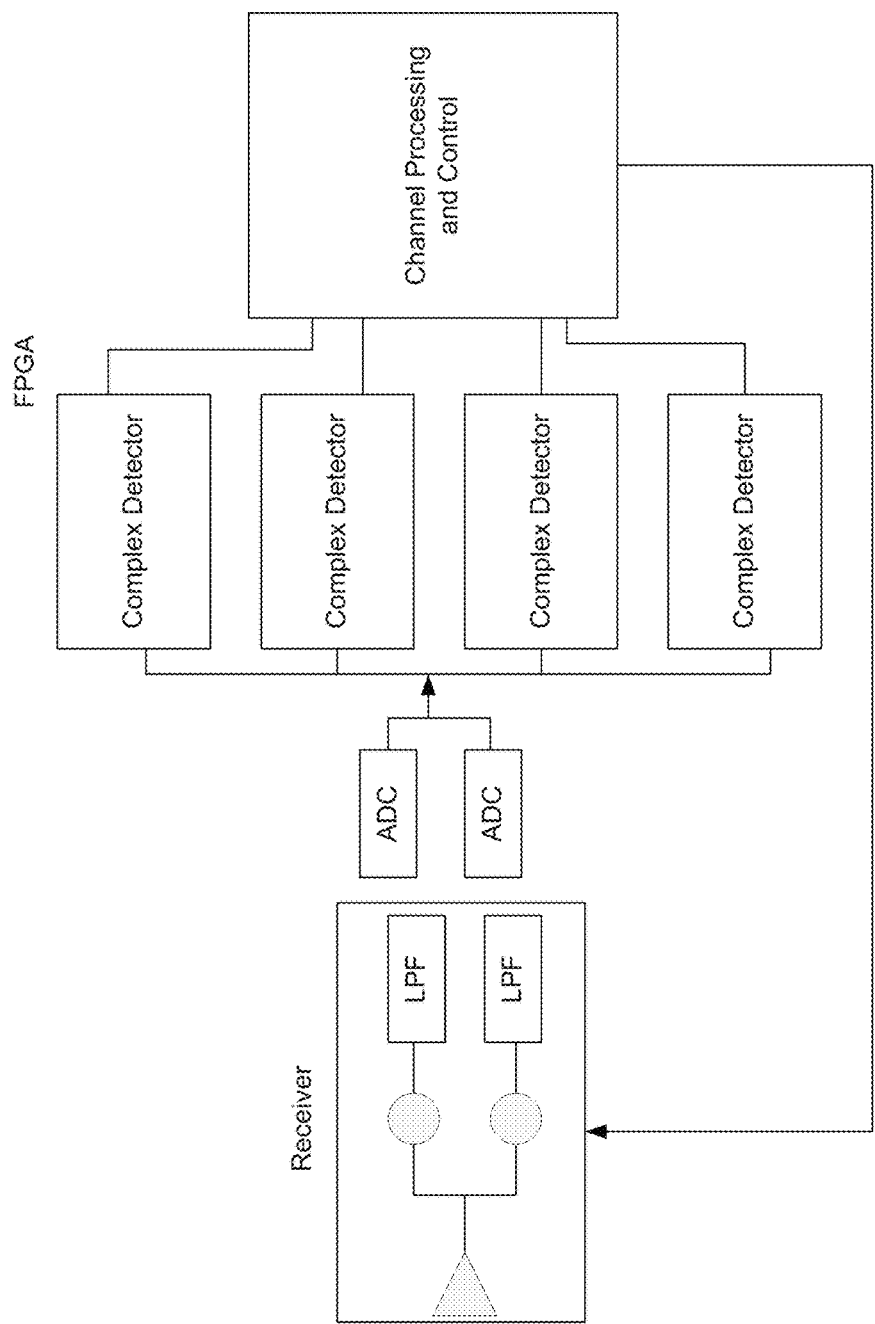
FIG. 9 illustrates an example broadcast receiver architecture for a compliance monitoring system.

FIG. 9 illustrates an example out-link receiver architecture. Referring to FIG. 9, the fine channels (the sub-region splitting of each region of the span into bins) can be processed in parallel. The receiver can scan coarse channels on command. The scan can be determined by frequency distribution. The receiver algorithm involves tuning to each major region with the front end receiver and then parallel processing of the fine divisions for possible detection events. This reduces the number of channel slots in the scan from 282 to 5 at the expense of reduced SNR and higher chance of potential collision in the multiple ingestion case. With enhancements to the broadcast communication protocol as described in more detail below, these limitations can be overcome.

The modulation format in combination with the out-link receiver strategy can improve multiple ingestion performance even further. If the bandwidth of the receive chains could be reduced, then the likelihood of collision in broadcast mode would be reduced or the number of frequency hops could be reduced. The modulation format (e.g., as shown in FIGS. 3 and 4) provides a long series of pulses at the start of a frame. Also, by design, the pulse spacing period is directly related to the broadcast frequency. For example, the ratio of pulse period (1 ms for example) to broadcast carrier period (2.5 ns for example) is exactly 400,000. If the carrier period increased by 10% then the pulse period would increase 10% to 1.1 ms. This can be measured by the receiver and used to retune to a carrier frequency of 363.636 MHz (1/2.75 ns). By measuring the pulse spacing during the start of the frame, the transmit frequency can be deduced and the detector bandwidths reduced accordingly. Reducing the bandwidth will reject other TAG transmissions in the vicinity. Several detection algorithms can be conceived that take advantage of the modulation format and spacing to carrier relationship.

To enable maximum detection rate, robust performance in all conditions, and operate efficiently in the case of multiple ingestions, a new communication protocol is proposed. This protocol actually exploits some of the limitations described above to enhance overall performance. The protocol supports three modes of operation:
1) Command mode: System depends on in-link signal and cannot operate in the absence of in-link
2) Broadcast mode: System does not require in-link and broadcasts data without external sync
3) Dual mode: Operates in command mode when in-link is present and in Broadcast mode when in-link is absent.

Figure 10:
FIG. 10 shows a sample base-frame data field for out-link.

Any protocol is responsible for transmitting data stored or sensed by the TAG. This data field may be of any length or definition. FIG. 10 shows a sample base-frame data field for out-link, representative of what may be found on a medical adherence device. The bit fields can be as follows:

START. The START field is fixed and indicates the beginning of the TAG data transmission.

GI. Battery voltage measured on chip and digitized. The least significant bit (LSB) is transmitted first.

NEXT ID. The random address generated on chip. This field indicates the next slot/bin the TAG will hop to. Reader may detect this and optionally respond in the in-link header with the same address to lock it "forever" on the TAG.

RSSI. The measured in-link signal strength. The LSB is transmitted first. The RSSI is logarithmic in nature.

TRACK ID. Programmed on TAG/CHIP. User defined field.

RID. Programmed on TAG/CHIP to associate with a user radio and mitigate alternate user interference.

PILL ID. Random address generated on chip. This field is set once upon power up and remains fixed for life of TAG. Used for multi-pill protocol.

END. The END field is fixed and indicates the end of the TAG transmission frame.

Of special note is the PILL ID and NEXT ID field. These are to support multiple pill ingestions. PILL ID is a random address generated once on power up. With multiple pills, this will allow each to be inventoried separately. The NEXT ID field is the location of the NEXT time or frequency hop to give advance notice to the out-link receiver where the next transmission slot will be. This permits continuity of message without the need for re-acquisition.

Figure 11A:
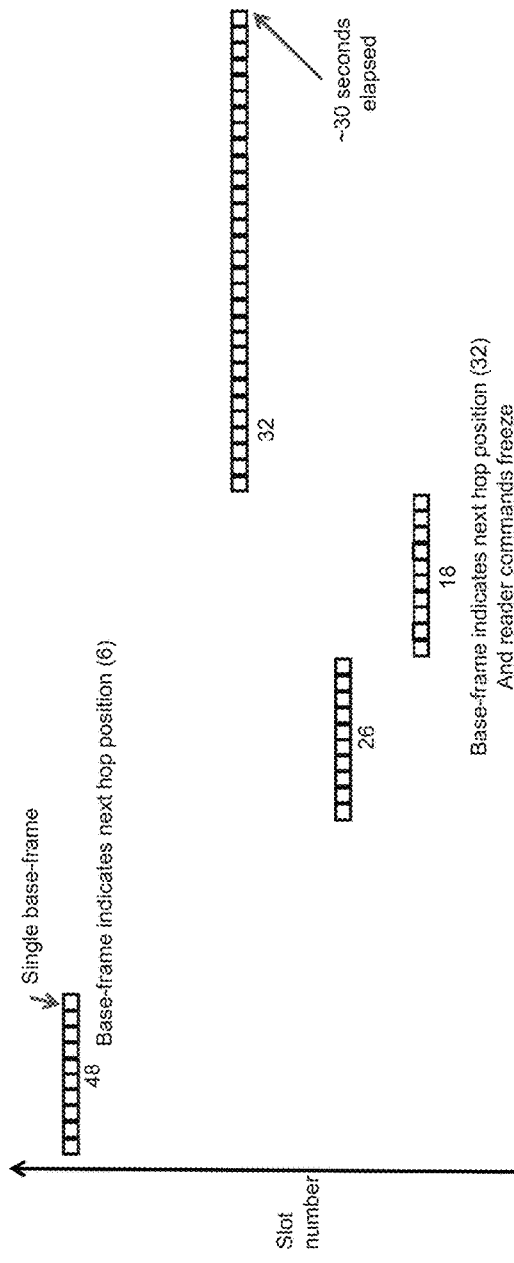
FIGS. 11A-11C illustrate the command mode protocol, the broadcast mode protocol, and the dual mode protocol, respectively.
Figure 11B:
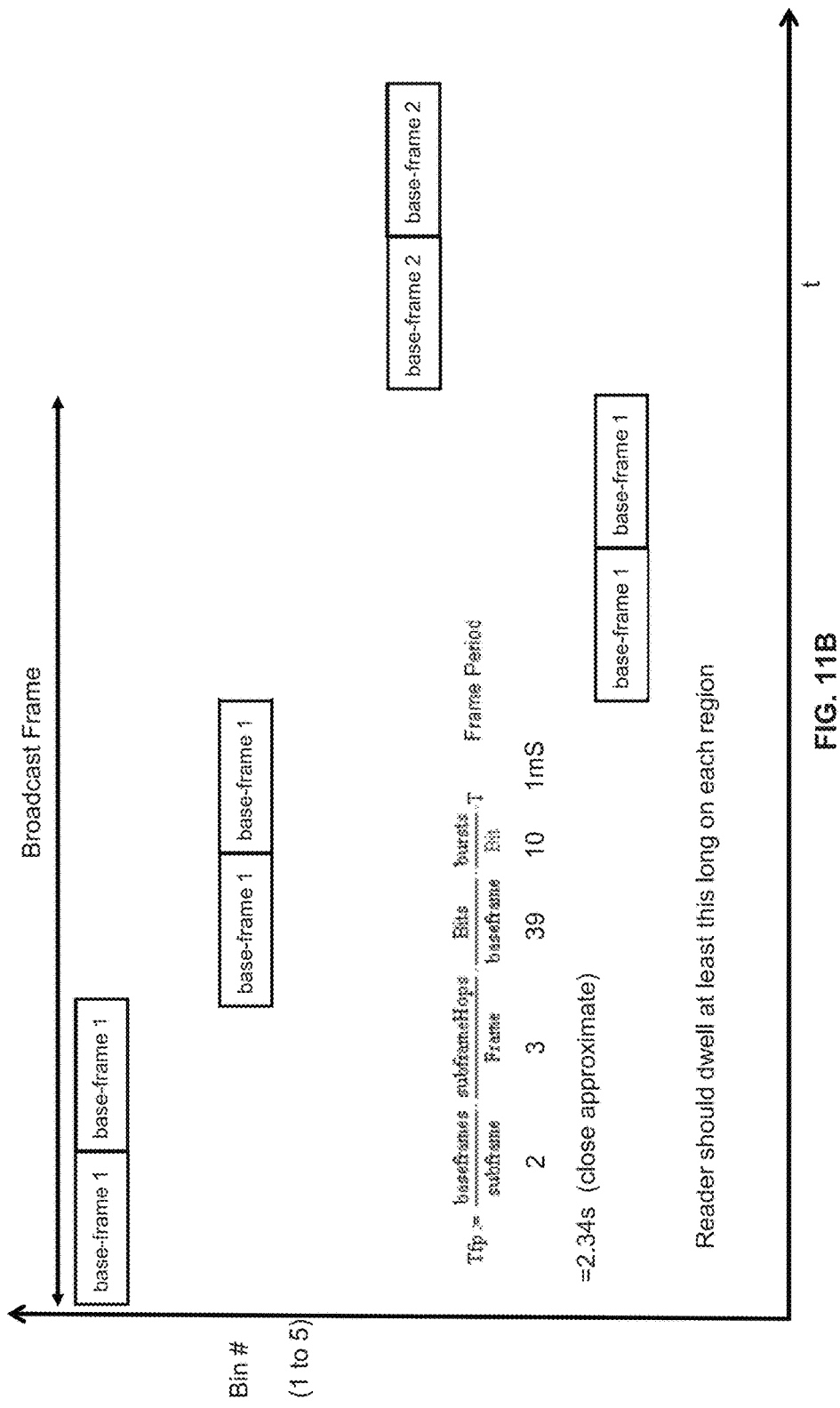
Figure 11C:
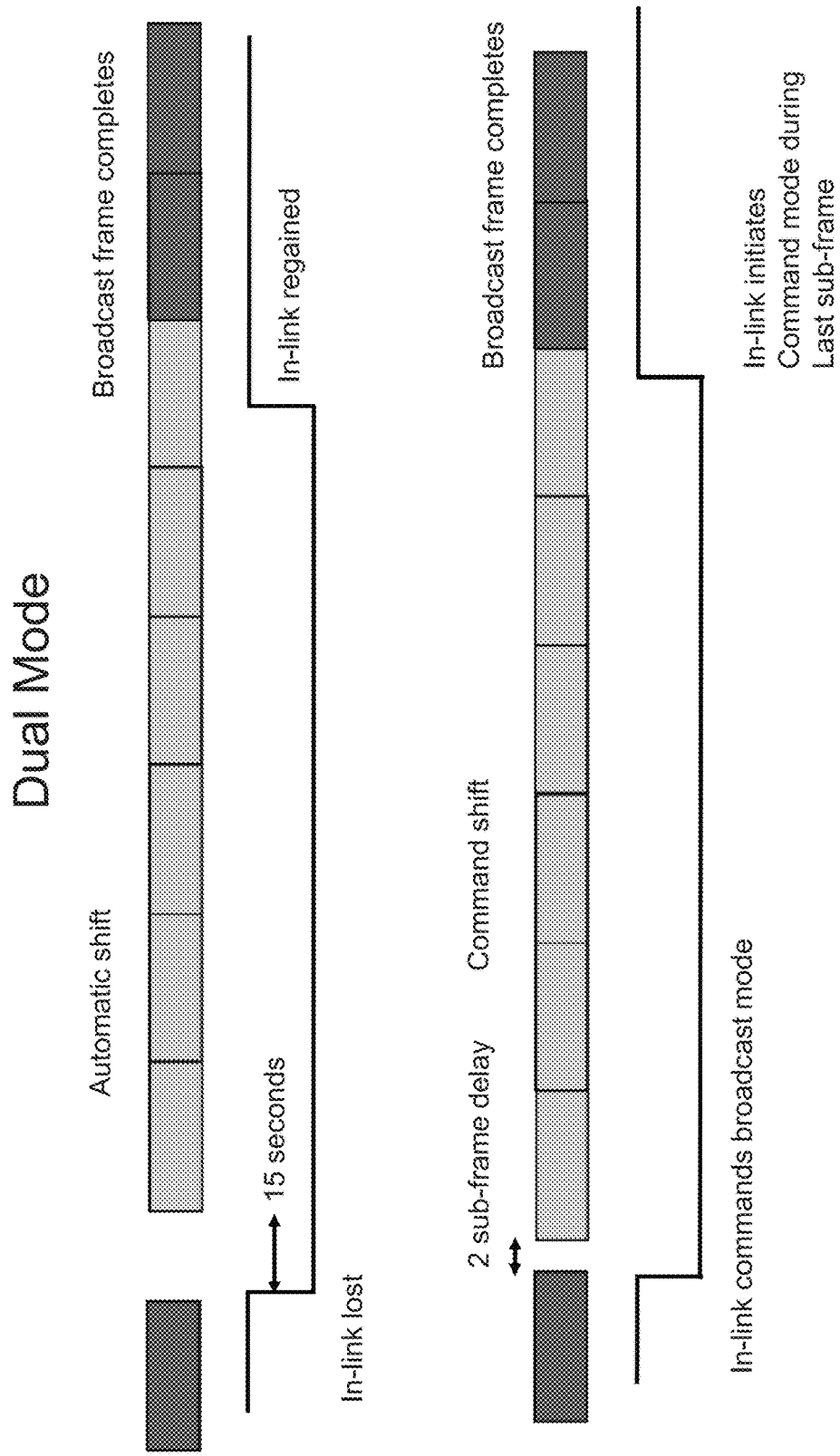

FIGS. 11A-11C illustrate the command mode protocol, the broadcast mode protocol, and the dual mode protocol, respectively.

Referring to FIG. 11A, for the command mode protocol, the base-frame is concatenated 10 times (or any other amount as desired). After transmission of 10 base-frames the TAG shifts to a new time slot to support multiple ingestions. This process repeats until the in-link signal commands the TAG to optionally freeze on a particular slot (slot 32 in the example) or continue to hop indefinitely.

Referring to FIG. 11B, for the broadcast mode protocol, 2 base-frames are concatenated and transmitted. This is followed by a frequency hop (limited to a span within a major region as defined in FIG. 5A). This process repeats (three times in this example) until a new base-frame begins the cycle anew.

The dual mode is a combination of command and broadcast modes. Referring to FIG. 11C, when the TAG is in this mode (as determined by program pins on the IC) the presence of an in-link signal will configure the TAG into the command mode. In the absence of an in-link signal the TAG will operate in broadcast mode. The TAG will convert to broadcast mode via two scenarios as shown in FIG. 11C. The first case is shown at the top of FIG. 11C. If in-link is lost for any reason, the TAG will attempt to re-acquire in command mode for a nominal time (15 seconds in this example). If after this time no in-link is sensed, then the TAG switches to broadcast mode. The TAG will remain in broadcast mode until in-link is restored. However, it will only switch back to command mode after a completed frame has been transmitted in broadcast mode. The second case is shown in the bottom of the FIG. 11C. In the case of a robust in-link environment, the TAG may be directed to enter broadcast mode but without the 15 second delay. Data within the in-link signal configures the delay of the TAG to be on the order of a base-frame length. Once this is programmed into the TAG the in-link is removed and the part enters broadcast mode. Once the in-link signal begins again, the TAG completes the broadcast mode of operation and enters command mode.

Not only is it beneficial to have a TAG that implements the above described protocols, but there should be a way to test the TAG to ensure that the TAG is properly manufactured. A medical adherence system must also be cost effective to be of practical benefit. Since a TAG is associated with each medical capsule or tablet ingested (medication carrier), the incremental cost of adding a TAG to each carrier must be kept as small as possible. Material costs for the TAG including the IC are minimized by reducing die size of the IC and creative use of low cost materials for TAG power generation and the antenna used to transmit the out-link signal. Of concern is the methodology used to validate that the TAG is functioning properly after encapsulation. Test time maps directly to test cost. Hence it is an object of this disclosure to present a test methodology for electronic adherence systems that supports a low cost model.

Since the TAG is powered by a weak electro-chemical battery or other harvested power source, the amount of energy available is extremely small. Average power dissipation of the TAG must be limited to roughly 50 µW or less. This ultimately leads to data transmission rates that are very slow. It may take 0.2 to over 1 second to transmit a frame of information. Once a TAG is encapsulated the only way to validate the TAG is functioning properly is to use the TAG telemetry system itself. However, in any ingestion, the TAG randomly comes up in only a few of the possible configurations. To test each possible configuration would take far longer than practical (possibly minutes). A means is necessary for the TAG to validate all possible combinations without the need to actually exercise each.

Figure 12:
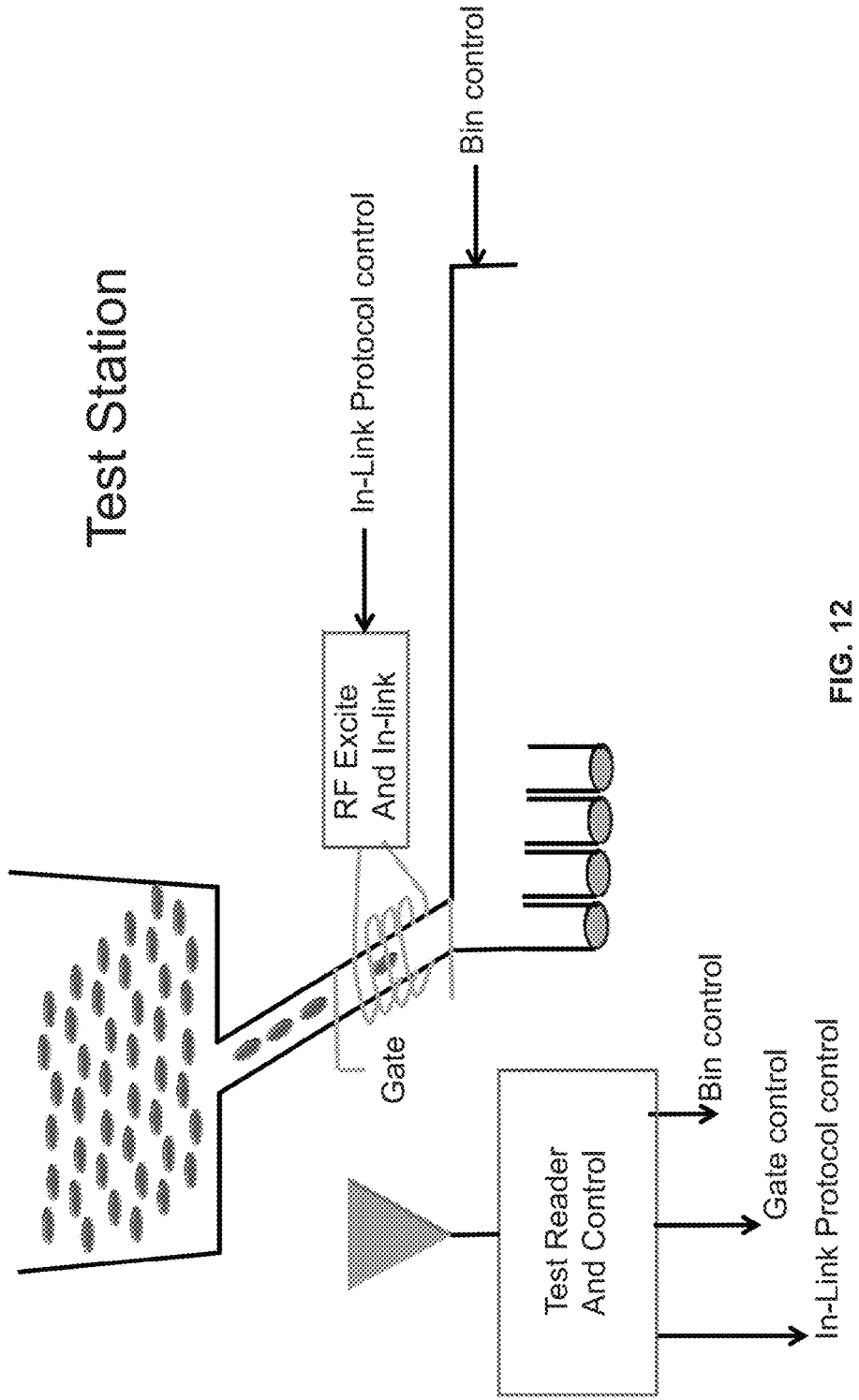
FIG. 12 illustrates an example test station.

TAG testing is essential in assuring robust and reliable medical adherence. Robust testing must also be very low cost in time and material. If millions or billions of TAGs are manufactured and tested the case is clear that test costs must be minimized. A test solution is disclosed which relies on the inherent functionality of the TAG electronics and associated communication protocol. Further, once a capsule is assembled, the described techniques operate to validate functionality without requiring electrochemical battery activation. A simple test station that is reproducible as product capacity increases facilitates a low cost solution. FIG. 12 illustrates an example test station. The test station can provide a fundamental platform to validate all assembled capsules containing an adherence TAG. Referring to FIG. 12, the capsules feed a test chute. The test chute includes a gate that is controlled to enable a single capsule to enter the test chamber. An RF field of sufficient strength is applied which is rectified on the TAG thereby producing TAG power. A custom test reader generates in-link and receives out-link signals from the capsule under test. The reader and test control then sorts the capsules into bins depending on test results.

To facilitate test, the TAG electronics can incorporate Built In Self Test (BIST) electronics that verify all digital electronics in the TAG. The TAG can then pass the results of the BIST via an out-link transmission. In some cases, the out-link base-frame field definitions may change from that described with respect to FIG. 10 to pass relevant BIST test results as desired. During test of the TAG, bits within the in-link data field configure the TAG into the test mode. The in-link can contain a data field that is frequency modulated. For example, when the TAG includes a phase locked loop (PLL) as described in application Ser. No. 14/573,315, which is hereby incorporated by reference, the reader can perform frequency modulation as also described in that Application. For example, the reader can frequency modulate a reference signal (e.g., a 4 MHz reference signal) with any required information or configuration data for the tag 15. If the tag PLL is locked (such as in response to the reader sending a signal to lock the TAG), the modulated data can directly be extracted from the VCO control voltage on the tag PLL and the TAG PLL can act as a demodulation block. The tag PLL then returns to the locked mode and stabilizes. When the PLL is given a command to frequency multiply the reference signal, the TAG generates a TX burst signal.

Figures 13A, 13B:
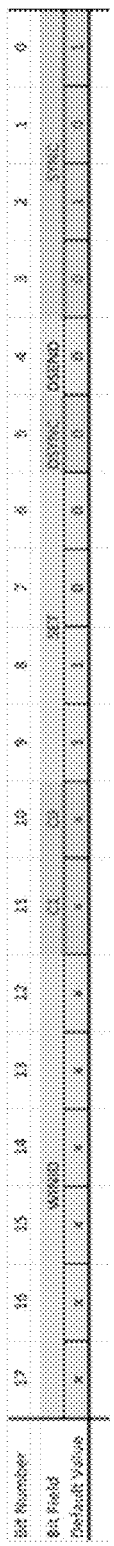
FIGS. 13A and 13B illustrate in-link data fields supporting dual mode and test protocol.

The in-link data field that supports the dual mode and test protocols is shown in FIG. 13A; and a further breakdown of bit definitions is shown in FIG. 13B for configuring test mode. While in test mode it is possible to send additional test vectors to assist the BIST operation if desired.

The bit fields can be as follows:

SYNC. The SYNC pattern is fixed and sent as depicted. These bits are used by the TAG to validate that a valid in-link signal has been transmitted.

DSEND. If DSYNC is set to 1, then DSEND initiates a single transmission frame. The Reader sets DSEND high for 1 header and resets to 0 for subsequent headers. After 1 frame, if DSEND is set high again, another frame is initiated. If DSYNC is 0, then DSEND has no affect and frames are transmitted periodically without interruption. In Dual Mode, the test is redefined as shown in FIG. 13B.

DSYNC. DSYNC determines if frame sync is desired. If DSYNC is equal to 1 then all tags will transmit only 1 frame when commanded by the DSEND bit. Otherwise, TAGs transmit periodically with no synchronization between TAGs if DSYNC is equal to 0. In Dual Mode, the test is redefined as shown in FIG. 13B.

SET. SET is dependent on C1, C0. The SET bits are used for IC configuration depending on configuration setting.

C0. Configuration bit

C1. C1 configures to normal (0) or production test (1). This bit controls whether the TAG will be in test mode.

WIN ID. The WIN ID is the TAG slot number. The Reader reads the random address the TAG sends. If WIN ID is set to this value, the proper TAG will respond by locking in that address. Alternatively, the Reader may send a fixed address until a TAG correlates to the address. In this fashion, the reader may force TAGs into specific slots.

Turning to FIG. 13B, certain modes can be controlled by C1 and C0. In the case illustrated in FIG. 13B, if C1 is equal to 0, regardless of the value for C0, the SET bits may tune broadcast TX frequency and DSYNC and DSEND are used for frame synchronization. If C1 is equal to 1 (indicating production test), regardless of the value for C0, the SET, DSYNC, and DSEND bits are used for test vector input.

Figure 14:
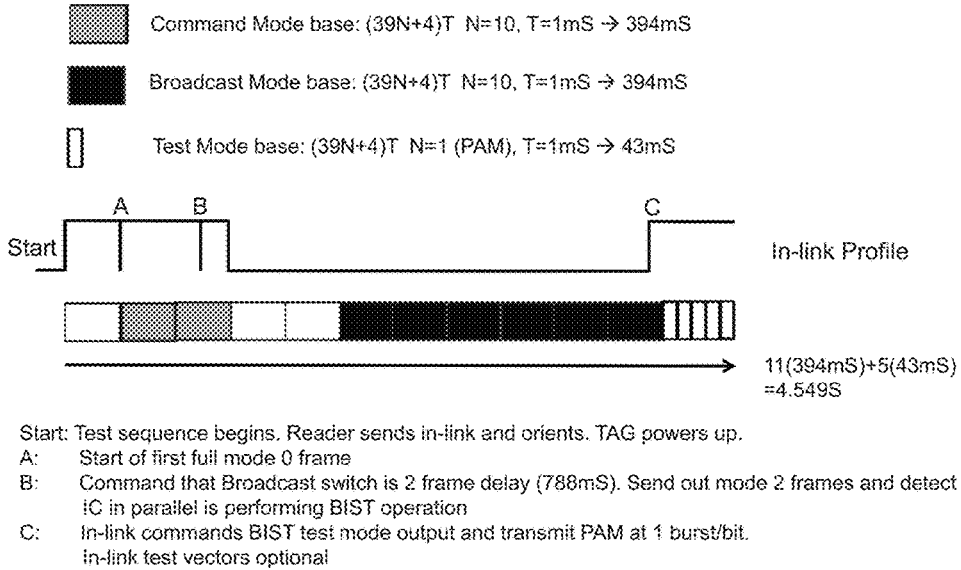
FIG. 14 shows an example test methodology and protocol.

FIG. 14 shows an example test methodology and protocol. Testing occurs in three phases. First, the TAG can be exercised in standard command mode to verify basic operation (A). This is followed by commanding the TAG to have only a 2 base-frame delay if in-link is lost. In-link is removed and the part should switch to broadcast mode. A full frame is sent with associated frequency hopping (B). During this sequence the TAG is performing a BIST on digital functions not checked during (A) and (B). After broadcast mode is checked the TAG sends out BIST data. Among this data is a flag that indicates if BIST passed. If the flag indicating BIST passed occurs, then the TAG is deemed good and binned accordingly (C). It should be mentioned that to reduce test time that the modulation format can be simple pulse amplitude modulation (PAM) with 1 burst per data bit. This reduces frame size leading to faster test times. This is possible because in the controlled test environment the SNR is so high that advanced modulation techniques are not necessary. The test reader records output power of the TAG and sets in-link to a minimum level expected in the body. Assuming the whole test sequence passes, the TAG is validated. This validates all analog and digital functions since the test could not succeed unless all components operate properly. The approach utilizes the intrinsic capability of the system to provide an efficient test method.

Figure 15:
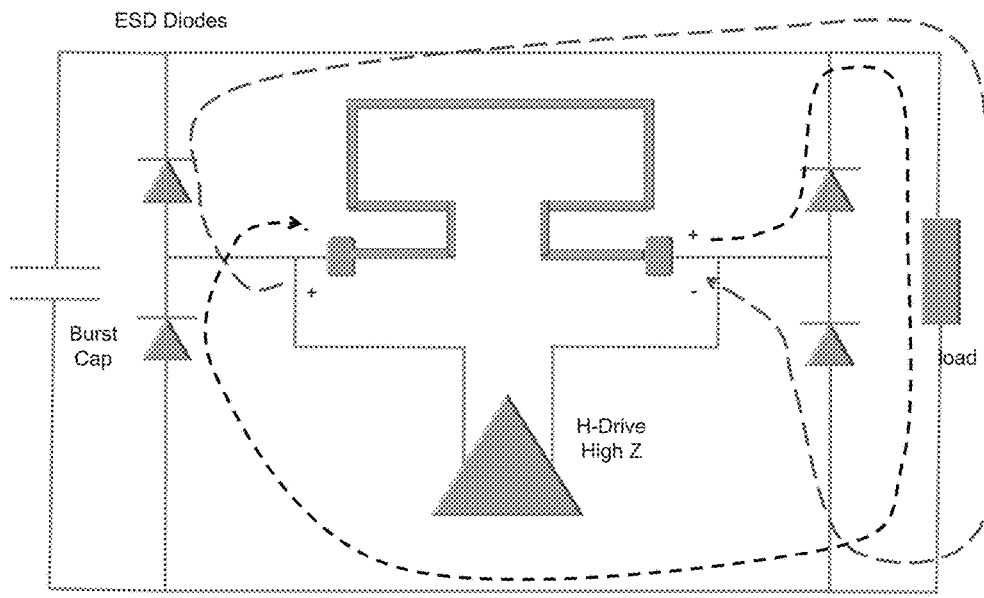
FIG. 15 shows a simplified TAG diagram illustrating the power source of the TAG for test.
Figure 16:
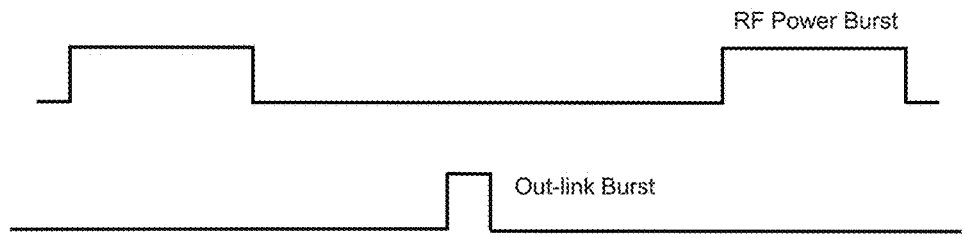
FIG. 16 illustrates an example excitation timing to enable the power source of the TAG for test.

To support the test capability, the TAG is powered without activating the battery. A simple method takes advantage of the fact that the TAG has an antenna for the out-link path. This antenna can also be used as a receive antenna for an external RF power source. The energy is harvested and rectified on chip, as shown in the simplified TAG diagram in FIG. 15. Since the out-link antenna is connected to the RF driver on the TAG, the driver is designed (required) to have a high impedance state when out-link is not present. The electro static discharge (ESD) protection diodes in place on the TAG IC can be used to rectify the external RF field. The external burst capacitor (provides energy when the TAG bursts) filters the rectified RF energy and supplies power for the entire IC. To eliminate conflicts when the out-link burst is present, the external field may be time multiplexed as shown in FIG. 16.

Implementation Examples

Figure 17:
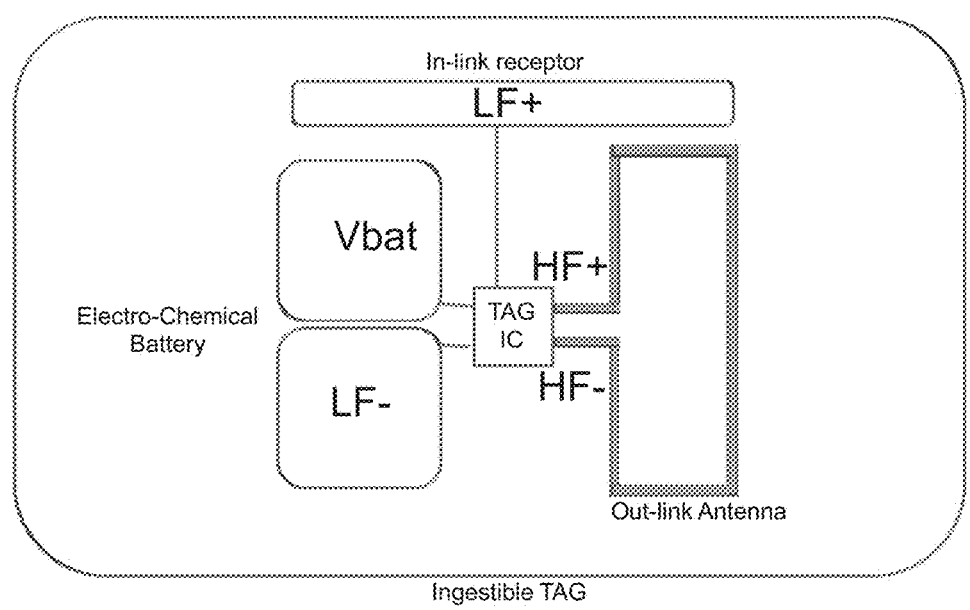
FIG. 17 shows a high level physical diagram of an example implementation of an ingestible TAG.

To implement the above described out-link TX symbol and communication protocols, the ingestible TAG is configured to generate the appropriate out-link signals and realize the communication protocols. FIG. 17 shows a high level physical diagram of an example implementation of an ingestible TAG. The TAG must sense the presence or absence of the in-link signal. In addition, the TAG must configure the out-link signal in command, broadcast, or dual mode, and provide the proper TX data format for those modes. This includes coding the data using the pulse reverse keyed (PRK) symbol, assuring a relationship between pulse spacing and carrier frequency, and generating the proper TX transmission frame. Referring to FIG. 17, the TAG includes positive and negative terminals of an electrochemical battery (Vbat, LF−), an in-link receptor pad (LF+), an Out-link antenna with connection ports (HF+, HF−), and a TAG integrated circuit (IC) which implements all of the required electrical functionality including symbol and protocol generation. Depending on implementation, other power sources may be used in place of the electrochemical battery and connected to the power terminal (having positive and negative terminals).

Figures 18A, 18B:
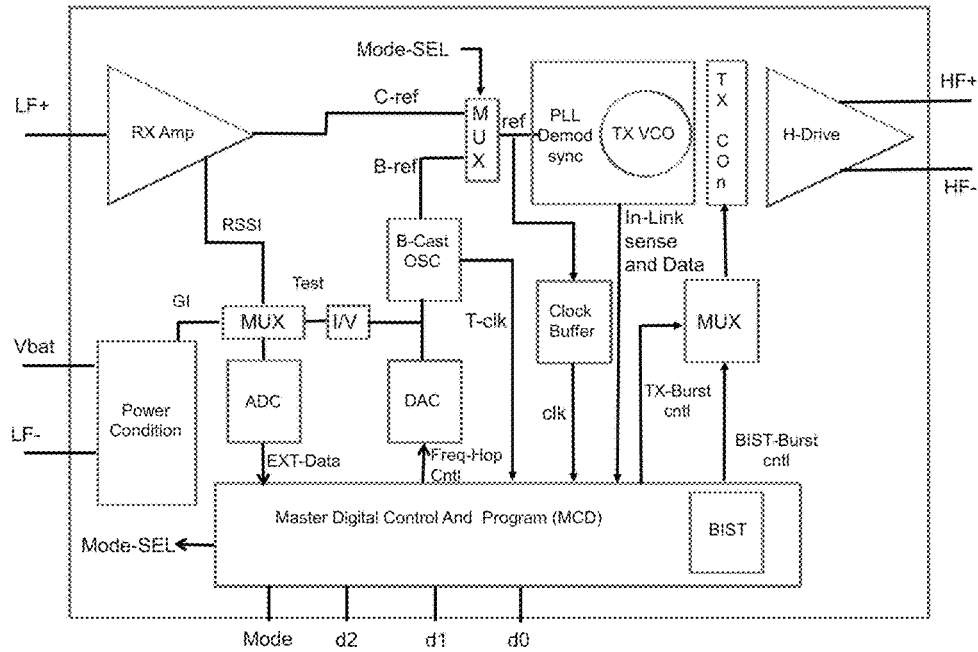
FIG. 18A shows a high level block diagram of an example TAG IC.
FIG. 18B shows definitions of interface pins to the TAG IC of FIG. 18A.

FIG. 18A shows a high level block diagram of an example TAG IC; and FIG. 18B shows definitions of interface pins to the IC. The Mode pin is used to configure the TAG into the one of command, broadcast, or dual mode operation. For example, if Mode is tied high (to Vbat) command mode is used, low (LF−) broadcast, and floating (no connection) would configure to dual mode. For most applications dual mode operation would be selected. Pins d0, d1, and d2 may be used to provide a simple chip ID by tying, low, high or float.

Figure 19:
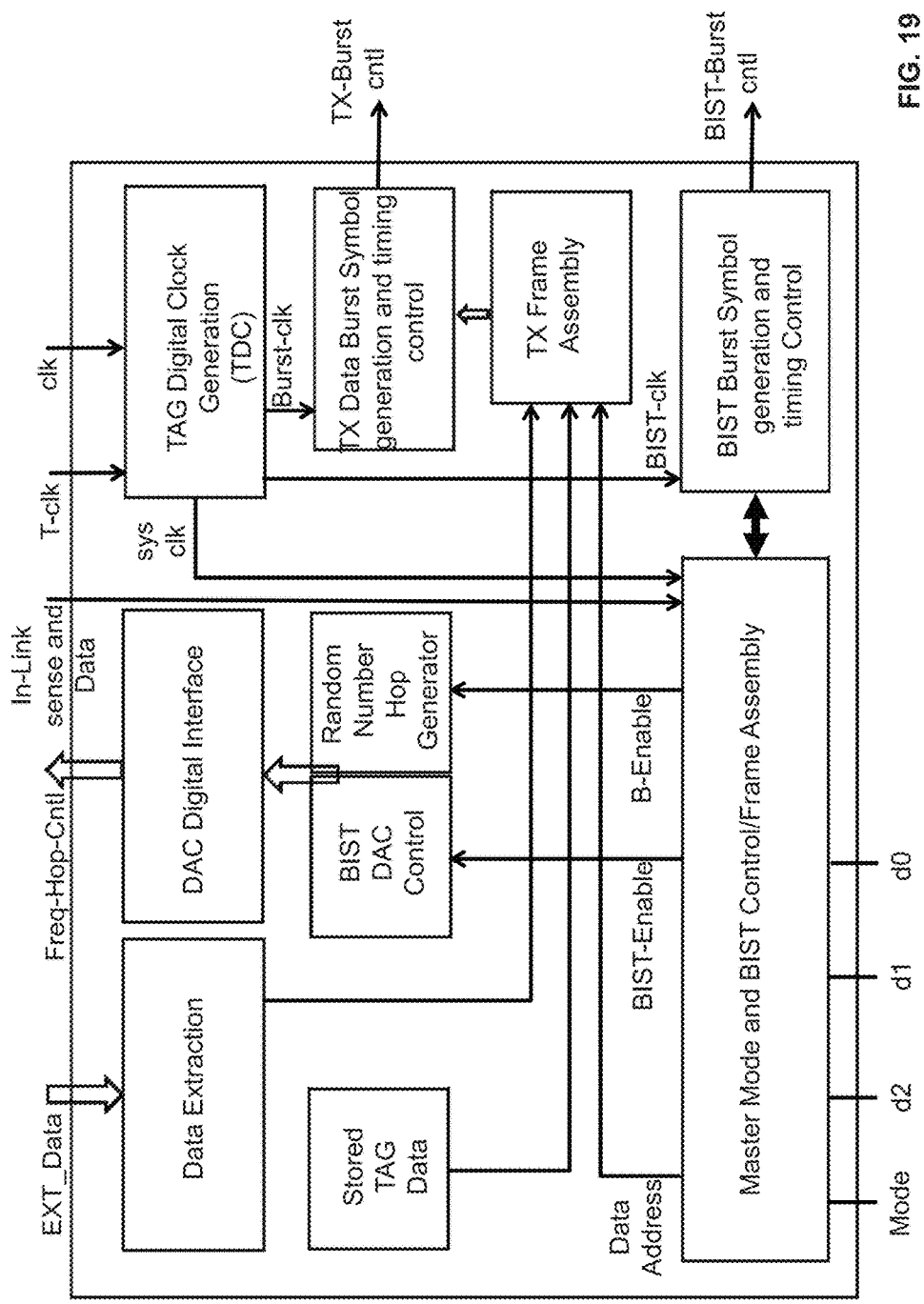
FIG. 19 shows a high level block diagram of an example Master Digital Control (MCD) for a TAG IC.

The TAG IC operates in one of three modes, controlled by the master digital control and program block (MCD) such as shown in FIG. 19. This MCD block is responsible for interpreting all external signaling and configuring the TAG appropriately. Configuration is simple if commanded by the mode pin to operate explicitly in command or broadcast mode. In dual mode, operation is more complex as the controller must sense when in-link is present. Each mode will briefly be described below.

Command Mode.

Command mode assumes the in-link signal is present. The in-link signal is received at LF+ and amplified by the RX Amp. A receive signal strength (RSSI) is derived and the extracted in-link signal (C-ref) is passed through the MUX to the PLL Demod sync block (Mode-SEL controls this as determined by the MCD). The in-link reference signal is nominally around 4 MHz in frequency. The PLL Demod block uses this reference to generate a phase locked and scaled carrier frequency 100× greater than the reference (typically 400 MHz). That portion of the in-link signal carrying configuration data is extracted and sent to the MCD (In-Link Data). It may be used for further chip configuration if desired. At the same time, the in-link signal (ref) is buffered and used as the main system clock within the MCD. Meantime, the MCD has generated a transmit control (TX-Burst cntl) composed of extracted battery and signal strength (GI and RSSI) and stored data on the IC including a self-generated address and non-volatile data such as patient ID or medication type. The TX-Burst cntl is essentially a gating signal used to modulate the carrier with the appropriate pulse reverse keyed (PRK) symbol based on data content. This gate is based on the symbol and communication protocol for command mode. Note that the gating sets the pulse spacing of the TX bursts and this is controlled by the MCD clock derived from the in-link signal (ref). Since this signal is phase locked to the TX carrier, there is a direct relationship between the carrier frequency and the pulse spacing as required by the protocol.

Broadcast Mode.

Broadcast mode assumes there is no in-link signal present. In this case the TAG IC generates all signals internally. Basically, all operation is the same as command mode except the in-link reference signal is replaced by an on-chip oscillator controlled by the MCD. This oscillator is then used to phase lock the out-link transmitter signal. Since the reference clock used within the MCD is still the same (although from a different source) as that used to generate the TX carrier, the requirement that pulse space and TX frequency be related is still achieved and thus the protocol requirement is still met. TX-Burst cntl is generated as in the broadcast case with the clear exception of the protocol differences (see description with respect to FIG. 11B). Symbol generation remains the same.

Dual Mode.

For dual mode operation, the MCD sets the Mode-SEL signal to switch between command and broadcast mode (see description with respect to FIG. 11C). It bases the determination primarily by the In-Link Data and sense information provided by the PLL Demod sync block. In dual mode the MCD is designed to seamlessly change clock domains between the in-link and on board oscillators. This is particularly critical in the case where in-link is lost and initial re-acquisition is attempted. In this situation the on-board oscillator is used to provide a temporary or transition clock (T-clk) while re-acquisition takes place. In this way, the in-link path may be maintained in order to continue the in-link search. Once the MCD determines that in-link has been satisfactorily recovered, the T-clk is replaced by clk.

The MCD and associated digital circuitry is used by the TAG to achieve the required protocol and symbol generation requirements. Referring to the example shown in FIG. 19, the TDC block generates all required clock using the clk and T-clk signals as reference. The TDC block will seamlessly generate these based on protocol requirements. The TDC block may include timers, gating logic, etc. The TX-Burst cntl and BIST-Burst cntl signals are generated by the associated blocks. The TX Data Burst Symbol generating and timing control (TBS) block uses assembled TX frame data and generates the proper PRK symbol for each data bit. The TBS block then sets the modulation gating based on the Burst-clk extracted from the TDC block. Since this clock was derived based on phase lock techniques, the requirement for pulse space and carrier frequency relationship is met by design. The TX frame assembly gathers both extracted and stored data as specified by an appropriate frame definition. This includes next slot hop information as required by the protocol. Similarly, when operated in test mode, the BIST-Burst cntl (such as described above with respect to understanding the in-link data fields for test mode) is properly generated.

To implement the broadcast protocol, the TX carrier should hop randomly within a frequency region. This is required in broadcast mode when the TX carrier is phase locked to the internal oscillator. The internal oscillator is a digitally controlled oscillator, with the oscillation frequency proportional to a digital control word. By varying a portion of this control word with a random value, a random frequency hop is generated. This is simply done using a random number generator as shown in the figure. In broadcast mode this value is passed to the oscillator based on the broadcast protocol.

Finally, when the unit is in test mode, the MCD controls all BIST functions as defined in the protocol. In order to test the DAC and ADC functions on the chip, a loopback path through the BIST DAC control is provided (see FIG. 18A as well). In this way all blocks of the chip may be tested and the results passed on through the BIST-Burst cntl and thus the out-link path.

It should be understood that the examples and embodiments described herein are for illustrative purposes only and that various modifications or changes in light thereof will be suggested to persons skilled in the art and are to be included within the spirit and purview of this application.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. An ingestible bio-telemetry communication network, comprising:
   each of a plurality of ingestible devices configured to obtain data relating to a patient, and transmit the data by bursting bits of the data with a selected gap between pulses in transmission to reduce power, wherein each pulse is repeated one or more times for a given data bit, and a burst pattern of the data is configured to have 50% or more burst density, wherein the pulses transmitted by each of the plurality of ingestible devices have a duty cycle of about 1 to 1000; and
   a receiver configured to be positioned outside the patient's body and receive the data.

2. The ingestible bio-telemetry communication network of claim 1, wherein each bit is represented by more than one (N) pulse slots, where a logic 1 bit is represented by N1 leading pulses and N0 trailing pulses, and logic 0 is represented by N0 leading pulses and N1 trailing pulses with empty pulse slots in between.

3. The ingestible bio-telemetry communication network of claim 1, wherein the data comprise one or more messages, each message comprising a set of bits and a frame sync sequence composed completely of pulses, wherein the receiver is configured to distinguish a start of each frame of the data based at least on the frame sync sequence without using a data correlator.

4. The ingestible bio-telemetry communication network of claim 1, wherein the selected gap between the pulses is determined based at least on a carrier frequency generated and used by each of the plurality of ingestible devices.

5. The ingestible bio-telemetry communication network of claim 4, wherein the selected gap is determined at least based on an on-chip clock of each of the plurality of ingestible devices generating the carrier frequency.

6. The ingestible bio-telemetry communication network of claim 1, wherein the receiver is configured to detect and use the selected gap between the pulses to determine one or more frequencies used by each of the plurality of ingestible devices.

7. An ingestible bio-telemetry system, comprising:
   a plurality of ingestible devices ingested by a patient, each of the plurality of ingestible devices operating at a frequency in transmitting a pulse sequence; and
   a reader device positioned outside the patient's body, wherein each of the plurality of ingestible devices and the reader device are configured to communicate with each other based at least on a communication protocol that allows for the reader device to fine tune a detection frequency of each of the plurality of ingestible devices by measuring a pulse period of each pulse sequence during detection, wherein the pulse period is proportional to a carrier frequency used by each of the plurality of ingestible devices, and wherein bursts transmitted by each of the plurality of ingestible devices have a duty cycle of about 1 to 1000 and 50% or more burst density.

* * * * *